United States Patent
Dubois (10) Patent No.: US 9,738,582 B2
(45) Date of Patent: Aug. 22, 2017

(54) PLATE-TYPE REACTOR WITH IN-SITU INJECTION

(71) Applicant: ARKEMA FRANCE, Colombes (FR)

(72) Inventor: Jean-Luc Dubois, Millery (FR)

(73) Assignee: ARKEMA FRANCE, Colombes (FR)

( * ) Notice: Subject to any disclaimer, the term of this patent is extended or adjusted under 35 U.S.C. 154(b) by 27 days.

(21) Appl. No.: 14/931,445

(22) Filed: Nov. 3, 2015

(65) Prior Publication Data

US 2016/0052853 A1 Feb. 25, 2016

Related U.S. Application Data

(62) Division of application No. 14/123,811, filed as application No. PCT/FR2012/051233 on Jun. 1, 2012, now Pat. No. 9,205,403.

(30) Foreign Application Priority Data

Jun. 6, 2011 (FR) ..................... 11 54885

(51) Int. Cl.
*B01J 19/00* (2006.01)
*B01J 19/24* (2006.01)
(Continued)

(52) U.S. Cl.
CPC .......... *C07C 45/512* (2013.01); *B01J 19/249* (2013.01); *C07C 41/01* (2013.01); *C07C 45/29* (2013.01);
(Continued)

(58) Field of Classification Search
CPC . B01J 19/00; B01J 19/24; B01J 19/248; B01J 19/249; B01J 2219/24; B01J 2219/245–2219/2453; B01J 2219/2455; B01J 2219/2459; B01J 2219/246; B01J 2219/2461; B01J 2219/2462; B01J 2219/2469; B01J 2219/247; B01J 2219/2476; B01J 2219/2477; B01J 2219/2481; C07C 41/00; C07C 41/01; C07C 45/00; C07C 45/27; C07C 45/29; C07C 45/32–45/35; C07C 45/51–45/512; C07C 51/00; C07C 51/347; C07D 307/00; C07D 307/02; C07D 307/34;
(Continued)

(56) References Cited

U.S. PATENT DOCUMENTS

2005/0020851 A1 1/2005 Olbert et al.
2005/0158217 A1 7/2005 Olbert et al.
(Continued)

FOREIGN PATENT DOCUMENTS

DE 10 2006 010 388 A1 9/2007
EP 0 995 491 A1 4/2000

*Primary Examiner* — Natasha Young
(74) *Attorney, Agent, or Firm* — Buchanan Ingersoll & Rooney P.C.

(57) ABSTRACT

A chemical reactor including: a plurality of heat exchange plates which between them define reaction compartments, in which reactor each heat exchange plate includes two walls between them defining at least one heat exchange space, the respective walls being fixed together by joining regions, and the reactor also comprises at least one injection device for injecting substance into the reaction compartments, said substance-injection device passing through the heat-exchange plates in respective joining regions thereof. Also, a chemical reaction process that can be carried out in this reactor.

7 Claims, 3 Drawing Sheets

(51) Int. Cl.

| | |
|---|---|
| *F28D 21/00* | (2006.01) |
| *F28F 9/00* | (2006.01) |
| *F28F 9/02* | (2006.01) |
| *C07C 45/00* | (2006.01) |
| *C07C 51/00* | (2006.01) |
| *C07D 307/00* | (2006.01) |
| *C07C 45/29* | (2006.01) |
| *C07C 45/35* | (2006.01) |
| *C07C 51/347* | (2006.01) |
| *C07C 45/51* | (2006.01) |
| *F28D 9/00* | (2006.01) |
| *C07C 41/01* | (2006.01) |
| *C07D 307/60* | (2006.01) |
| *C07D 307/89* | (2006.01) |
| *C07C 45/27* | (2006.01) |
| *C07C 45/32* | (2006.01) |
| *C07C 45/33* | (2006.01) |
| *C07C 45/34* | (2006.01) |

(52) U.S. Cl.
 CPC ............ *C07C 45/35* (2013.01); *C07C 51/347* (2013.01); *C07D 307/60* (2013.01); *C07D 307/89* (2013.01); *F28D 9/0043* (2013.01); *F28F 9/027* (2013.01); *B01J 2219/246* (2013.01); *B01J 2219/247* (2013.01); *B01J 2219/2453* (2013.01); *B01J 2219/2455* (2013.01); *B01J 2219/2459* (2013.01); *B01J 2219/2462* (2013.01); *B01J 2219/2481* (2013.01); *F28D 2021/0022* (2013.01)

(58) Field of Classification Search
 CPC .. C07D 307/56; C07D 307/60; C07D 307/77; C07D 307/87; C07D 307/89; F28D 9/00; F28D 9/0031; F28D 9/0043; F28D 21/00; F28D 2021/0019; F28D 2021/0022; F28F 9/00; F28F 9/02; F28F 9/026; F28F 9/027
 See application file for complete search history.

(56) References Cited

U.S. PATENT DOCUMENTS

| | | |
|---|---|---|
| 2005/0226793 A1 | 10/2005 | Sakakura et al. |
| 2006/0276334 A1 | 12/2006 | Balduf et al. |
| 2010/0189609 A1 | 7/2010 | Barbieri et al. |

PLATE-TYPE REACTOR WITH IN-SITU INJECTION

CROSS-REFERENCE TO RELATED APPLICATIONS

This application is a divisional application of U.S. application Ser. No. 14/123,811, now U.S. Pat. No. 9,205,403, filed on Dec. 4, 2013, which is a National Stage Application under 35 U.S.C. §371 of International Application No. PCT/FR2012/051233, now WO 2012/168631, filed on Jun. 1, 2012, which claims the benefit of French application No. FR 1154885, filed on Jun. 6, 2011. The entire contents of each of U.S. application Ser. No. 14/123,811, International Application No. PCT/FR2012/051233, and French application No. FR 1154885 are hereby incorporated herein by reference in their entirety.

TECHNICAL FIELD

The present invention relates to a chemical reactor exhibiting a geometry of plate type which makes possible the in situ injection of a substance, such as oxygen, into the reaction medium, optionally in multi-staged fashion. The invention also relates to a chemical reaction process using said reactor.

TECHNICAL BACKGROUND

The use of chemical reactions, in particular involving heterogeneous catalysis, in fixed bed reactors is known. When these chemical reactions are highly endothermic or highly exothermic, control of the heat absorbed or emitted by the reaction presupposes that the reactor has available extensive heat-exchange surfaces.

For example, a conventional geometry of fixed bed chemical reactors is the multi-tubular geometry. This geometry exhibits in particular the disadvantage of involving relatively complex and lengthy operations for charging and discharging catalyst which result in losses in productivity. Furthermore, multi-tubular reactors exhibit a very high manufacturing cost but also a very high weight related to the masses of metals which it is necessary to use. Another constraint on these reactors is related to their method of manufacture and transportation: they are limited in size as, manufactured and tested in a factory, they subsequently have to be transported to the site of final use.

Another geometry known for these reactors is the plate geometry. In a plate reactor, the reaction compartments are delimited by heat-exchange plates. The documents EP 0995491 and EP 1147807 provide examples of such plate reactors.

Another example appears in the document US 2005/0020851, which describes such a reactor used for the oxidation of a $C_3$ or $C_4$ precursor to give acrolein, methacrolein, acrylic acid or methacrylic acid.

The document US 2005/0158217 also describes a reactor of this type, in which thermocouples are positioned in the reaction compartments (without passing through them) in order to control the reaction.

The document US 2005/0226793 describes a specific arrangement of heat-exchange plates, in which arrangement the projections of each plate are facing the reinforcements of the adjacent plate and vice versa, in order to improve the control of the temperature.

Finally, the document US 2006/0276334 provides another example of a reactor of this type, in which the heat-exchange plates comprise a cracked coating (deposit).

All the above reactors exhibit the disadvantage of not making possible sufficient control/management of the temperature in the reactor, in the reaction phase and/or in the regeneration phase.

There thus exists a real need to make possible better control of the temperature in fixed bed reactors.

SUMMARY OF THE INVENTION

The invention relates first to a chemical reactor comprising a plurality of heat-exchange plates defining, between them, reaction compartments, in which reactor each heat-exchange plate comprises two walls defining, between them, at least one heat-exchange space, the respective walls being fixed to one another by joining regions, and the reactor also comprises at least one device for injection of substance into the reaction compartments, said substance-injecting device passing through the heat-exchange plates in respective joining regions of the plates.

According to one embodiment, the substance-injecting device is a device for the injection of gas and preferably a device for the injection of oxygen-comprising gas.

According to one embodiment, the substance-injecting device is a pipe exhibiting a plurality of injection orifices.

According to one embodiment, the joining regions are positioned on the heat-exchange plates in the form of strips, preferably parallel strips, or in the form of points.

According to one embodiment, the chemical reactor comprises a plurality of substance-injecting devices, preferably parallel to one another and preferably connected to a substance-distributing system.

According to one embodiment, the heat-exchange plates are positioned in a chamber in a radial manner or in a manner parallel to one another and are preferably grouped into modules.

The invention also relates to a chemical reaction process comprising the admission of reactants at the inlet of a reaction compartment defined between two heat-exchange plates, the withdrawal of reaction products at the outlet of the reaction compartment, and the injection of a substance into the reaction compartment, in which process each heat-exchange plate comprises two walls defining, between them, at least one heat-exchange space, the respective walls being fixed to one another by joining regions, and the injection of substance being carried out by means of at least one substance-injecting device which passes through the heat-exchange plates in respective joining regions of the plates.

According to one embodiment, the reaction is of the heterogeneous catalytic type and a catalyst is positioned in the reaction compartments, preferably in the form of solid particles.

According to one embodiment, the process alternately comprises phases of production and phases of regeneration of the catalyst, the injection of substance being carried out during the reaction phases and/or during the regeneration phases.

According to one embodiment, the substance is a reactant or a catalytic compound or a compound capable of regenerating a catalyst.

According to one embodiment, the substance is an oxygen-comprising gas.

According to one embodiment, the substance is injected at several points of the route of the reactants in the reaction compartment.

According to one embodiment, the process is carried out in a chemical reactor as described above.

According to one embodiment, the process is:
- a process for the dehydration of glycerol to give acrolein; or
- a process for the dehydration of lactic acid to give acrylic acid; or
- a process for the dehydration of 3-hydroxypropionic acid to give acrylic acid; or
- a process for the dehydration of 3-hydroxyisobutyric acid to give methacrylic acid; or
- a process for the dehydration of 2-hydroxyisobutyric acid, also known as alpha-hydroxyisobutyric acid, to give methacrylic acid; or
- a process for the preparation of a hydrofluoroolefin or of a hydrofluorocarbon, preferably a process for the preparation of a fluoropropene and very particularly preferably a process for the preparation of 2,3,3,3-tetrafluoropropene.

The present invention makes it possible to overcome the disadvantages of the state of the art. It more particularly provides a fixed bed reactor in which the control of the temperature at any point of the reactor is improved.

This is accomplished by virtue of a plate reactor geometry, in which an injection of a substance in situ into the reaction compartments is carried out by means of injection devices which pass through the plates. This injection makes it possible to exert better control over the chemical processes in the combined reaction compartments by modifying the composition of the reaction stream or the reaction conditions in situ.

According to certain specific embodiments, the invention also exhibits one or preferably several of the advantageous characteristics listed below.

The invention is particularly appropriate for the implementation of reactions in which the catalyst is susceptible to deactivation by coking and has to be regenerated by combustion. This is because, by choosing an oxygen-comprising gas as substance injected in situ, it is possible to carry out the regeneration much more rapidly, with a better homogeneity in temperature in the reactor. Furthermore, the risks of explosion or runaway are limited by avoiding a high oxygen partial pressure at the inlet of the reactor.

The invention makes it possible to achieve an increase in yield of the order of several percent. The invention also makes it possible to limit the down times of the reactor for regeneration and thus to obtain an increase in productivity typically of the order of 25% to 100%.

DESCRIPTION OF EMBODIMENTS OF THE INVENTION

The invention is now described in more detail and without limitation in the description which follows.

General Description of the Reactor

Figure 1:
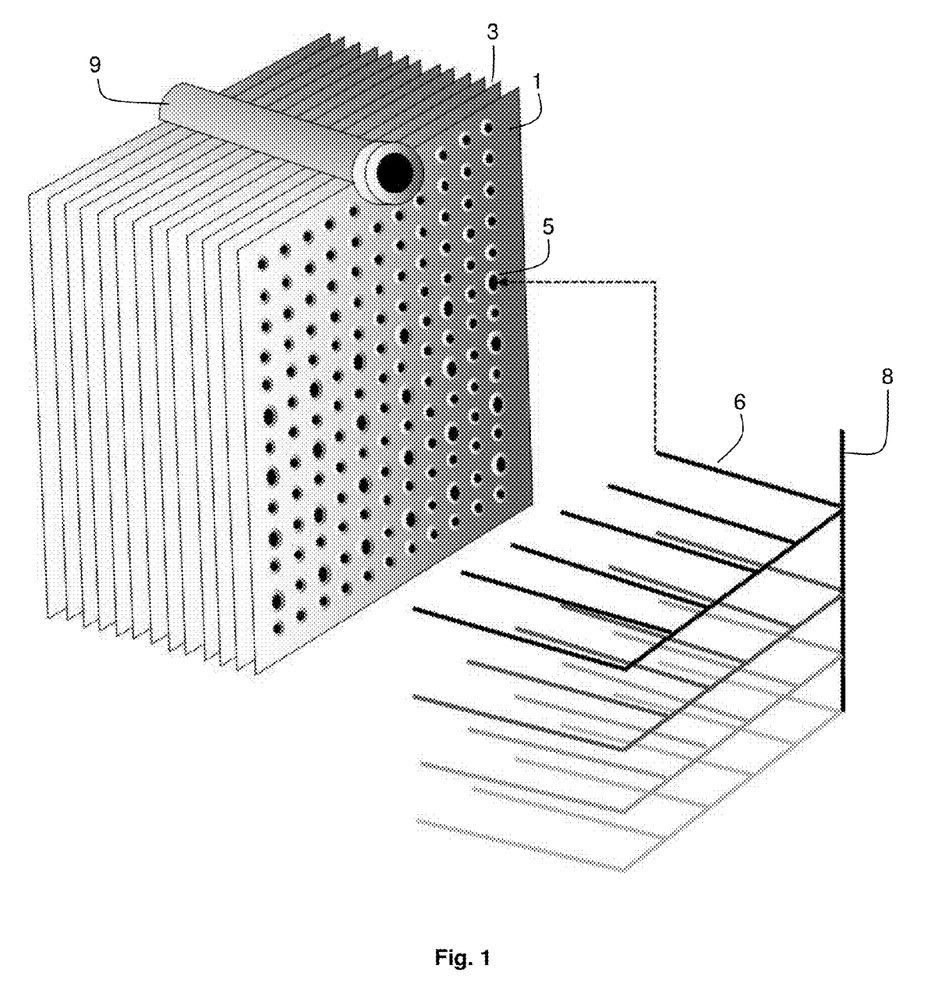
FIG. 1 represents, in perspective and in exploded view, a portion of a reactor according to one embodiment of the invention.
Figure 2:
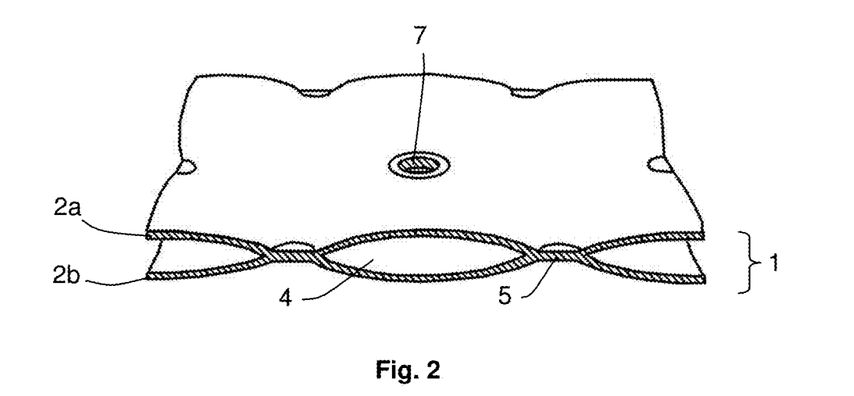
FIGS. 2 and 3 represent, in perspective and in section, details of a heat-exchange plate in a reactor according to one embodiment of the invention.
Figure 3:
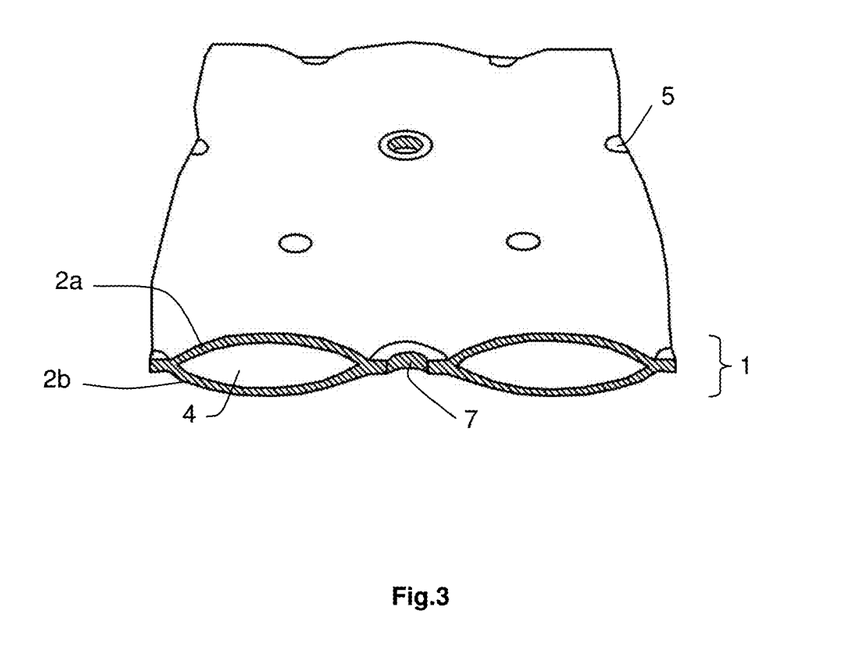
Figure 4:
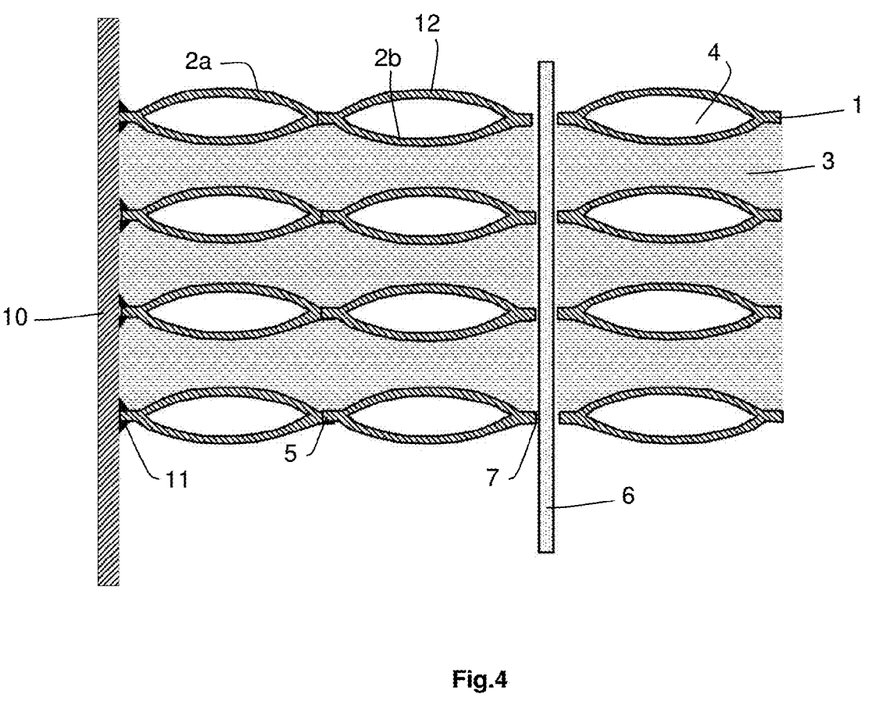
FIG. 4 represents a section of a portion of a reactor according to one embodiment of the invention.

With reference mainly to FIGS. 1 and 4, generally, the reactor according to the invention comprises a chamber, which is advantageously essentially cylindrical with a circular section, inside which is positioned an assembly of heat-exchange plates 1 delimiting, between them, reaction compartments 3.

The reaction compartments 3 are advantageously filled with a catalyst appropriate for the reaction carried out, this catalyst preferably being in the form of solid particles (beads, grains or powder) or in the form of porous monolith or of blocks of porous monolith.

The reactor can operate according to at least two modes, namely a production mode, during which the targeted chemical reaction takes place in the reaction compartments; and a regeneration mode, during which the at least partially deactivated catalyst is regenerated.

In the context of the present patent application, the expression "reaction stream" is understood within the broad sense and denotes a stream passing through the reaction compartments 3, it being understood that the composition of the reaction stream varies between the inlet and the outlet of the reaction compartments 3.

In the production phase, the reaction stream at the inlet of the reaction compartments 3 comprises all or part of the reactants (it being possible for another part of the reactants optionally to be introduced via the substance-injecting devices described below) and the reaction stream at the outlet of the reaction compartments 3 comprises, at least in part, the products of the reaction.

In the regeneration phase, the reaction stream at the inlet of the reaction compartments 3 can comprise one or more compounds capable of regenerating the catalyst, and the reaction stream at the outlet of the reaction compartments 3 comprises residues from the regeneration. Alternatively, the reaction stream at the inlet of the reaction compartments 3 can be a simple inert stream (it being possible for the compounds capable of regenerating the catalyst to be injected by means of the substance-injecting devices 6 described below).

In comparison with a multi-tubular geometry, a plate geometry exhibits a greater simplicity of manufacture, of use and of maintenance.

Each heat-exchange plate 1 defines a mean plane. The term "length" denotes the dimension of the plates 1 in this plane along the main axis of the chamber of the reactor (cylindrical axis in general) and the term "width" denotes the dimension of the plates 1 orthogonal to the preceding dimension in this same plane.

Generally, the axis of the chamber of the reactor is positioned along the vertical direction. This implies that the length of the plates 1 is along the vertical direction and that the width and the thickness of the plates 1 are along horizontal directions.

The width of the plates 1 is generally dictated by manufacturing considerations; it can, for example, be from 100 to 2500 mm and in particular from 500 to 1500 mm. The length of the plates 1 depends on the reaction and in particular on its temperature profile. It can, for example, be from 500 to 7000 mm and in particular from 3000 to 4000 mm.

According to one embodiment, the heat-exchange plates 1 are positioned according to a radial arrangement in the chamber. Such a radial arrangement is described, for example, in the document US 2005/0226793, in connection in particular with FIG. 6. This arrangement makes possible optimum use of all of the chamber of the reactor, when the chamber is cylindrical with a circular cross section.

According to an alternative embodiment to the above, and which is preferred in order to simplify and render uniform the flow of the reaction stream, the heat-exchange plates 1 are positioned essentially parallel to one another, so that the reaction compartments 3 are volumes with an overall uniform thickness (apart from the local deformation of the heat-exchange plates 1).

In this case, in order to make possible better use of the space available in the chamber, it can be advantageous to divide up the heat-exchange plates 1 and the interposed reaction compartments 3 into reaction modules of rectangular parallelepipedal form. Such an arrangement of the heat-exchange plates 1 into modules is described, for example, in the document US 2005/0020851, in particular in connection with FIGS. 1A, 1C, 1D, 1E and 1F.

Such a modular structure can make it possible to adapt the reactor in a flexible manner with regard to the capacity required, for example by installing only a portion of the modules in the reactor, in order to adjust the capacity thereof, or by closing some modules in order to isolate them from the reaction stream.

The modules can have the same dimensions, which simplifies the manufacture thereof. They can also have different dimensions, in order to optimize the occupation of the space in the chamber of the reactor.

Preferably, the modules can be individually withdrawn, replaced or exchanged, which simplifies the maintenance operations.

Each module is preferably held in position and stabilized in the chamber by an appropriate guide, for example a rectangular frame 10, to which the plates 1 of the module can be fixed by fixing means 11. The guides or frames 10 of the various modules can be sealed from one another to prevent any flow from one module to the other.

The intermediate space located between the wall of the chamber and the adjacent module or modules can be separated from the reaction compartments 3 by sealing (and optionally by filling with inert materials and by pressurization), in order to prevent any reaction or accumulation of material in this region.

Various possible forms of installing the modules in the chamber and of sealing the assembly are described in detail in the document US 2005/0020851.

With reference mainly to FIGS. 2 to 5, each heat-exchange plate 1 is formed of two walls 2a, 2b, between which at least one heat-exchange space 4 is arranged. The walls 2a, 2b can, for example, consist of sheets of stainless steel, generally of rectangular shape. The thickness of the walls 2a, 2b can, for example, be from 1 to 4 mm, in particular from 1.5 to 3 mm and especially from 2 to 2.5 mm.

The two walls 2a, 2b are fixed to one other by joining regions 5. This fixing can be carried out, for example, by welding the walls 2a, 2b to one another. The joining regions 5 can be of any shape.

According to one embodiment, the joining regions 5 are in the form of points (as is the case in FIGS. 1 to 4).

The term "points" is understood here to mean joining regions 5 exhibiting a relatively small size with respect to the total size of the heat-exchange plate 1, this being the case both in the direction of the length and in the direction of the width of the heat-exchange plate 1.

By way of example, each joining region 5 of point type exhibits a width of less than or equal to 5% or of less than or equal to 1% or of less than or equal to 0.5% of the total width of the plate, and also a length of less than or equal to 5% or of less than or equal to 1% or of less than or equal to 0.5% of the total length of the plate 1.

Thus, the "point-form" joining regions 5 can preferably have a circular/discal shape but also optionally a polygonal shape (for example, shape of squares).

When the joining regions 5 are in the form of "points" within the meaning of the present patent application, these points can be distributed according to a two-dimensional network over each heat-exchange plate 1, for example a network having a rectangular mesh or having a square mesh; or according to a hexagonal paving, for example.

According to a specific embodiment, the joining regions 5 in the form of points are distributed in parallel lines, the spacing between the successive joining regions within one and the same line being, for example, from 30 to 80 mm, or from 35 to 70 mm, or from 40 to 60 mm. In addition, the lines of points are preferably equidistant, with a separation between lines, for example, of 5 to 80 mm, or of 8 to 70 mm, or of 10 to 60 mm. The successive lines of points can be offset with respect to one another along the direction of the lines, for example by half a spacing between points of one and the same line. In other words, in this case, the points of the lines are in orthogonal alignment to the lines in a proportion of one line out of two.

Figure 5:
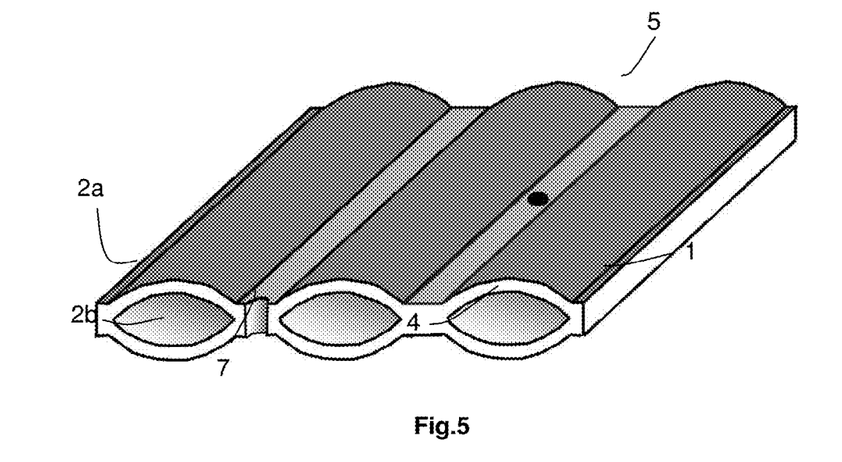
FIG. 5 represents, in perspective and in section, details of a heat-exchange plate in a reactor according to another embodiment of the invention.

According to another embodiment represented in FIG. 5, the joining regions 5 are in the form of strips, that is to say of lines. The strips can be curved or, preferably, straight. The (successive) adjacent strips are preferably parallel to one another and, for example, equidistant. These strips can, for example, be positioned in the direction of the length of the heat-exchange plates 1 or along their width. By way of example, the distance between strips can be from 100 to 1500 mm and preferably from 400 to 1000 mm, when they are arranged in the direction of the length of the reactor, and from 5 to 2000 mm and preferably from 40 to 120 mm, when they are arranged in the direction of the width of the reactor.

When the joining regions 5 are in the form of points, the heat-exchange space 4 between the walls 2a, 2b of the heat-exchange plate 1 is generally a single space. On the other hand, when the joining regions 5 are in the form of strips, the heat-exchange space 4 between the walls 2a, 2b of the heat-exchange plate 1 is generally composed of a plurality of channels delimited by successive joining regions 5.

It should be noted that it is possible to combine joining regions 5 in the form of points with joining regions 5 in the form of strips.

In addition to the joining regions 5 described above, the walls 2a, 2b of each heat-exchange plate 1 are advantageously joined to one another or sealed at their periphery in order to confine the heat-exchange fluid in the heat-exchange space 4. Preferably, this joining or this sealing is not complete, in order to insert at least one opening for the entry of the heat-exchange fluid into the heat-exchange space 4 and at least one opening for the departure of the heat-exchange fluid.

Generally, a heat-exchange fluid is circulated in the heat-exchange space 4 of each plate 1 in order to introduce heat into the reaction compartments 3 (case of an endothermic reaction) or in order to remove heat from the reaction compartments (case of an exothermic reaction). The heat-exchange fluid can also be a mineral oil or a synthetic oil, for example a Jarytherm or a Dowtherm. The heat-exchange fluid can also be a mixture of molten nitrates and/or nitrites, for example a eutectic mixture of sodium nitrate, potassium nitrate and sodium nitrite, having a low melting point and a high heat capacity. Preferably, the heat-exchange fluid is used for purposes of removal of heat.

The heat-exchange fluid can in particular be an aqueous solution optionally comprising additives, such as hydrazine or ammonia or a corrosion inhibitor. The circulation of the heat-exchange fluid in the heat-exchange spaces 4 can be of cocurrent or countercurrent or transverse (crossed) type, with respect to the circulation of the reaction stream in the adjacent reaction compartments 3.

For optimum heat transfer, the heat-exchange fluid partially changes in state during its passage through the heat-exchange space 4; for example, it changes at least partially from the liquid state to the vapor state in the case of an exothermic reaction.

In order to make possible the presence of the heat-exchange fluid in the heat-exchange spaces 4, the walls 2a, 2b of the heat-exchange plates 1 are deformed (swollen) at a distance from the joining regions 5. In other words, each heat-exchange plate 1, in use, comprises portions of minimum thickness (or depressions) at the joining regions 5 of the walls 2a, 2b, and portions of maximum thickness (or protuberances 12) at a distance from the joining regions 5 of the walls 2a, 2b.

It is possible to position the joining regions 5 on the plates 1 and to align the successive heat-exchange plates 1 so that the protuberances 12 of the respective plates 1 are aligned and that the depressions of the respective plates 1 are aligned orthogonally to the plates. Such an arrangement facilitates the installation of the substance-injecting devices 6 described below, perpendicularly to the plates 1.

However, it is also possible to position the joining regions 5 on the plates 1 and to align the successive heat-exchange plates 1 so that the protuberances 12 of the respective plates 1 are offset and that the depressions of the respective plates 1 are offset. For example, the protuberances 12 of each plate 1 can be aligned with the depressions of its neighboring plate or plates 1 orthogonally to the plates 1 and vice versa. Such an arrangement makes it possible to reduce the variations in thickness of the reaction compartments 3. The document US 2005/0226793 provides an example of an arrangement of this type. In the context of the invention, this arrangement requires, however, that the substance-injecting devices 6 described below be positioned in an inclined manner with respect to the direction orthogonal to the plates 1, which can complicate the design of the reactor.

Typically, the minimum thickness of the reaction compartments 3 (that is to say, the thickness at the point or at the points where the adjacent plates are the least spaced out) is from 8 to 150 mm, for example from 10 to 100 mm, in particular from 12 to 50 mm, especially from 14 to 25 mm and, by way of illustration, from 16 to 20 mm. In any case, the thickness of the reaction compartments 3 has to be adapted in order to be able to fill the reaction compartments 3 with the catalyst, which is, for example, in the form of grains. The catalyst grains generally have a size (Dv50) of 1 to 10 mm, for example of approximately 5 mm. It is desirable for the thickness of the reaction compartments 3 to be of the order of 3 to 5 grains at least, in order to be able to easily fill them. Use may also be made of the catalyst forms as monolithic blocks with a thickness of 20 mm, for example.

It is also possible to provide reaction compartments 3 with different thicknesses within the reactor.

The reaction compartments 3 can be isolated from one another by sealing or else they can be in communication via their ends.

Spacing elements can be provided between the successive heat-exchange plates 1, in order to limit the deformations of the plates 1 and the relative displacements of the plates 1.

A system for distributing heat-exchange fluid and a system for collecting heat-exchange fluid are provided on either side of the heat-exchange plates 1. It is possible, for example, to provide a modular distribution system and a modular collecting system.

The heat-exchange fluid can circulate naturally or in forced fashion in the heat-exchange spaces 4. In this second case, pumping means can be provided at the inlet.

Thermal expansion joints can be provided on the chamber (at the periphery and/or at the ends of the latter). The abovementioned distribution systems advantageously exhibit curved or angular portions which make it possible to compensate for the thermal expansion.

A system for distribution of reaction stream 9 and a system for collecting reaction stream (not represented) are provided on either side of the reaction compartments 3. It is possible, for example, to provide a modular distribution system and a modular collecting system. The reaction stream can be of liquid or gaseous or mixed type. The reaction stream can circulate from the top downward or from the bottom upward with respect to the chamber.

Catalyst-retaining means (typically perforated plates) are provided at the inlet and at the outlet of the reaction compartments 3.

It is possible to provide baffling in the reaction compartments 3 and/or in the heat-exchange space 4, in order to force the heat-exchange fluid and/or the reaction stream to flow along a predetermined route.

Injection of Substance In Situ into the Reaction Compartments

The invention provides at least one substance-injecting device 6 in the reaction compartments 3, preferably a plurality. The substance-injecting devices 6 pass through the heat-exchange plates 1 and the reaction compartments 3 between the heat-exchange plates 1.

According to the embodiment illustrated in the figures, which is particularly simple to implement, the substance-injecting devices 6 are substance-injecting pipes 6, essentially parallel to one another and preferably orthogonal to the heat-exchange plates 1.

The substance-injecting pipes 6 can, for example, be manufactured from stainless steel or from porous ceramic.

The substance-injecting pipes 6 pass through the heat-exchange plates 1 at the joining regions 5 described above. Thus, any risk of communication between the heat-exchange spaces 4 occupied by the heat-exchange fluid and the reaction compartments 3 occupied by the reaction stream is avoided.

To do this, the joining regions 5 have to exhibit dimensions which are sufficient to allow an opening 7 to be drilled within these joining regions 5 without compromising the leak-tightness of the heat-exchange space 4, the opening 7 being appropriate for the passage of the substance-injecting pipe 6.

The substance-injecting pipes 6 have, for example, a diameter of 10 to 100 mm and preferably of 20 to 50 mm (in order for them to have sufficient stiffness to allow assembling). The joining regions 5, which consist, for example, of welds of circular shape, preferably exhibit, at their center, respective openings 7 with a diameter slightly greater (for example from 1 to 5 mm) than that of the substance-injecting pipes 6.

Sealing means can be provided around the substance-injecting pipes 6 at the openings 7 on the joining regions 5 if it is desired to prevent any communication between reaction compartments 3.

Furthermore, each substance-injecting pipe 6 comprises substance-injecting means, which can be simple orifices, preferably over the whole of its length passing through the reaction compartments 3.

All of the substance-injecting pipes 6 can be connected to at least one substance-distributing system 8 (itself connected to a supply of substance to be injected). It is possible to provide substance-distributing systems which are independent between the modules or a single substance-distributing system for all of the modules. Optionally, at least one substance-collecting system (not represented) or several, for example one per module, is/are also provided at the opposite end of the substance-injecting pipes 6 with respect to the substance-distributing system(s) 8. This proves to be useful when it is desirable for only a portion of the substance stream circulating in the pipe 6 to pass into the reaction compartments 3 which have been passed through (for example in order to guarantee a sufficient pressure at any injection point).

When the joining regions 5 are in the form of points, it is possible to provide a substance-injecting device 6 which passes through each joining region 5, or else it is possible to provide substance-injecting devices 6 which pass through only some joining regions 5, the other joining regions 5 then preferably being devoid of opening 7: it is this embodiment which is represented in FIGS. 1 to 4.

When the joining regions 5 are in the form of strips, it is possible to provide a substance-injecting device 6 which passes through each strip, or else it is possible to provide substance-injecting devices 6 which pass through only some strips, the other strips then preferably being devoid of opening 7. It is also possible to provide several substance-injecting devices 6 which pass through one and the same strip, the latter being drilled with a number of openings appropriate for the number of substance-injecting devices 6 passing through it.

Preferably, the arrangement of the substance-injecting devices 6 makes possible an essentially homogenous injection of the substance into the reaction compartments 3.

The substance injected into the reaction compartments 3 by means of the substance-injecting devices can be a gas or a liquid or a mixture of the two.

It can be a reactant or a catalytic compound or a compound capable of regenerating the catalyst present in the reaction compartments 3.

It is possible to inject substance into the reaction compartments 3 solely during the production phase or solely during the regeneration phase or during both phases.

It is also possible to inject different substances over time (for example, a first substance when the reactor operates in the production phase and a second substance when the reactor operates in the regeneration phase).

Preferably, the substance injected is an oxygen-comprising gas, for example virtually pure oxygen, or air, or a mixture of inert gas and oxygen.

This is because, for the reactions in which the catalyst is deactivated by coking, the injection of oxygen during the regeneration phase makes it possible to carry out combustion and thus regeneration of the catalyst, this being carried out with better control of the temperature in all the reaction compartments and with greater safety. In particular, it is thus possible to avoid displacement of hot front through the entire catalyst bed. In addition, the injection of oxygen during the production phase can make it possible to extend the duration of deactivation of the catalyst, still with the abovementioned benefits in terms of improved control of the temperature and safety.

The injection of oxygen is also of use for the catalysts, the regeneration of which involves an oxygenation, such as, for example, catalysts of bismuth molybdate type used for the oxidation of propylene to give acrolein and of isobutene/t-butanol to give methacrolein, or catalysts of iron molybdate type used for multiple reactions, such as the oxidation of methanol to give formaldehyde, the oxidation of ethanol to give acetaldehyde, the oxidation of methanol to give dimethoxymethane, the oxidation of ethanol to give diethoxyethane, and the like.

Another example of substance injected is chlorine, in particular in the context of the implementation of fluorination reactions. This is because the injection of chlorine in the production phase makes it possible to inhibit reactions in which the catalyst is deactivated.

If required, the stream of the injected substance can be adjusted differently according to the injection sites. Pumping or compressing means and valves make it possible to regulate the flow rate of substance in each substance-injecting device 6 and in each reaction compartment 3.

Reactions which can be Carried Out According to the Invention

The invention is advantageously employed for the production of acrylic acid of renewable origin, in particular the production of acrylic acid from glycerol, comprising a first stage of dehydration of the glycerol to give acrolein, followed by a stage of oxidation in the gas phase of the acrolein thus obtained; or in the production of acrylic acid by dehydration of 2-hydroxypropionic acid (lactic acid) or 3-hydroxypropionic acid and their esters.

The invention makes it possible in particular to carry out a process for the dehydration of glycerol to give acrolein. In this type of process, the glycerol is fed in the form of an aqueous solution with a concentration of 20 to 95% by weight. The more concentrated the glycerol, the greater the tendency of the catalysts to form coke, which necessitates regularly regenerating the catalyst. According to the process described in the application WO 2006/087083, the reaction is advantageously carried out in the presence of oxygen, the addition of oxygen to the reaction for the dehydration of glycerol making it possible to extend the lifetime of the catalyst and to space out the regenerations.

The reaction is typically carried out at a temperature of 220 to 350° C. and preferably of 280 to 320° C., and at a pressure varying from atmospheric pressure to a few bar (for example 5). The concentration of the reactants is in part dictated or imposed by the flammability limits. In the reactors of the prior art, the flammability limits of an $O_2$/inert gas/glycerol/steam gas mixture prescribe a low concentration of glycerol and oxygen in the gas phase.

With the reactor of the invention, it is possible to employ a mixture which is richer in glycerol than with the reactors of the prior art, as additional oxygen is introduced by injection in situ. For example, it is possible to use mixtures comprising 6% of glycerol and from 1 to 2% of oxygen, the remainder being introduced in situ.

The catalysts which can be used for this reaction are acid catalysts, in particular having a Hammett acidity of less than +2, such as described, for example, in the documents EP 1 848 681, WO 2009/12855, WO 2009/044081 or WO 2010/046227. Many acid catalysts may be suitable for this reaction. Mention will be made of phosphated zirconias, tungstated zirconias, silica zirconias, titanium or tin oxides impregnated with tungstate or phosphotungstate or silicotungstate, phosphated aluminas or silicas, heteropolyacids or heteropolyacid salts, iron phosphates and iron phosphates comprising a promoter.

In the context of this process, the catalyst undergoes deactivation, in particular by coking. However, this deactivation can be delayed by the injection of oxygen in situ into the reaction compartments of the reactor, in the production phase. The $O_2$/glycerol molar ratio at the reactor inlet is from 0.1 to 1.5 (preferably from 0.3 to 1.0) and the oxygen partial pressure is less than 7%. The addition of supplementary oxygen, in the form of molecular oxygen, of air or of a mixture of oxygen and a gas which is inert for the reaction, is distributed over the length of the reactor. Preferably, between 2 and 10 injection sites are provided over the length of the reactor. The cumulative partial pressure of the oxygen added along the reactor is thus from 1 to 10%.

Furthermore, in the regeneration phase, the injection of oxygen in situ into the reaction compartments of the reactor makes it possible to regenerate the catalyst in a safe and controlled manner.

Generally, in the regeneration phase, it is necessary to properly control the temperature of the catalyst in order to prevent conditions for runaway of the reaction, resulting in very high rises in the temperature of the catalyst which can irreversibly damage it and even damage the reactor. The aim is thus to limit the temperature which the catalyst can reach by very greatly diluting the gas stream and/or by adding inert heat-exchange compounds, such as steam or $CO_2$. The regeneration then takes a great deal of time as a hot front moves through the catalyst bed corresponding to the combustion of the coke. It is thus desirable to accelerate the reaction for regeneration by combustion of the coke. This regeneration can be accelerated by increasing the temperature and/or the oxygen partial pressure but there is then a risk of encountering the disadvantages listed above. The reactor of the invention makes it possible to space out the addition of oxygen at several points of the reactor and consequently to carry out a regeneration while multiplying the hot fronts in the reactor. It is thus desirable to inject the oxygen in multiple lines and preferably with lines spaced out every 5% to 33% of the length of the reactor and preferably 10% to 20% of the length of the reactor.

The invention also makes it possible to carry out a process for the dehydration of lactic acid or 3-hydroxypropionic acid (and their corresponding esters) to give acrylic acid.

Lactic acid has a boiling point in the vicinity of 217° C. and 3-hydroxypropionic acid has a boiling point of 279° C. (calculated value). The flammability limits for lactic acid in air are 3.1% (lower limit) and 18% (upper limit). The methyl ester of lactic acid has a boiling point of 145° C., for the flammability limits of 1.1% and 3.6% (which gives greater flexibility of use than for the acid). The methyl ester of 3-hydroxypropionic acid has a boiling point of 179° C. (180° C. as calculated value). The ethyl ester of lactic acid has a boiling point of 154° C. and flammability limits of 1.6% and 10.6%. The ethyl ester of 3-hydroxypropionic acid has a boiling point of 187.5° C.

For these reactions, use is made of a reactor configuration substantially identical to that for the dehydration of glycerol. The dehydration conditions are a temperature of 220 to 400° C. and preferably of 250 to 350° C. and a pressure of 0.5 to 5 bar.

The catalysts which may be suitable for these reactions are acid catalysts, having in particular a Hammett acidity of less than +2. The catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts comprising in particular at least one element chosen from the group consisting of W, Mo and V. Mention may particularly be made, among mixed oxides, of those based on iron and on phosphorus and of those based on cesium, phosphorus and tungsten.

Other catalysts which may also be suitable for these reactions are obtained from phosphates and/or sulfates of alkali metals, alkaline earth metals and rare earth metals, and their mixtures. This group thus includes lanthanum phosphates and oxyphosphates, sodium phosphates, calcium phosphates, calcium sulfate, magnesium sulfate, and the corresponding hydrogenphosphates, aluminum phosphate, boron phosphate. All the above mentioned active materials can be impregnated or coated on any type of support, such as: alumina, titanium oxide, zirconium oxide or silica, but also the corresponding mixed oxides, and silicon carbide.

The lactic acid or 3-hydroxypropionic acid partial pressure is generally from 1% to 10% and preferably from 2% to 6%.

Still in the context of these reactions, the catalyst undergoes deactivation, in particular by coking. This deactivation can be delayed by injecting oxygen in situ into the reaction compartments of the reactor, in the production phase. The conditions relating to the injection of oxygen are the same as those described above in connection with the dehydration of glycerol.

Furthermore, in the regeneration phase, the injection of oxygen in situ into the reaction compartments of the reactor makes it possible to regenerate the catalyst in a safe and controlled manner. The conditions relating to the injection of oxygen are the same as those described above in connection with the dehydration of glycerol.

The invention also makes it possible to carry out a process for the dehydration of 2-hydroxyisobutyric acid or 3-hydroxyisobutyric acid to give methacrylic acid.

For this type of reaction, use is made of a reactor configuration substantially identical to that for the dehydration of glycerol. The dehydration conditions are a temperature of 200 to 400° C., and preferably of 250 to 350° C. and a pressure of 0.5 to 5 bar. The catalysts which may be suitable for this reaction are acid catalysts, having in particular a Hammett acidity of less than +2. The catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts comprising in particular at least one element chosen from the group consisting of W, Mo and V. Mention may particularly be made, among mixed oxides, of those based on iron and on phosphorus and of those based on cesium, phosphorus and tungsten.

Catalysts which may also be suitable for this reaction are obtained from phosphates and/or sulfates of alkali metals, alkaline earth metals and rare earth metals, and their mixtures. This group thus includes lanthanum phosphates and oxyphosphates, sodium phosphates, calcium phosphates, calcium sulfate, magnesium sulfate, and the corresponding hydrogenphosphates, aluminum phosphate, boron phosphate. All the above mentioned active materials can be impregnated or coated on any type of support, such as: alumina, titanium oxide, zirconium oxide or silica, but also the corresponding mixed oxides, and silicon carbide.

The (2- or 3-)hydroxyisobutyric acid partial pressure is generally from 1% to 10% and preferably from 2% to 6%.

Still in the context of these reactions, the catalyst undergoes deactivation, in particular by coking. This deactivation can be delayed by injecting oxygen in situ into the reaction compartments of the reactor, in the production phase. The conditions relating to the injection of oxygen are the same as those described above in connection with the dehydration of glycerol.

Furthermore, in the regeneration phase, the injection of oxygen in situ into the reaction compartments of the reactor makes it possible to regenerate the catalyst in a safe and controlled manner. The conditions relating to the injection of oxygen are the same as those described above in connection with the dehydration of glycerol.

The invention also makes it possible to carry out selective oxidations, such as the oxidation of methanol to give formaldehyde or dimethoxymethane; the oxidation of ethanol to give acetaldehyde or diethoxyethane; the oxidation of ortho-xylene or naphthalene to give phthalic anhydride; or the oxidation of benzene, butene, butanol or butane to give maleic anhydride.

In these oxidation reactions, the shared problem is that of injecting, at the reactor inlet, a sufficient amount of oxygen (or other oxidizing agent) to ensure complete conversion or at least the highest possible conversion of the hydrocarbon reactant while making sure to limit the risks of runaway of the reactor and the risks of explosion. The solution selected comes down to limiting the productivity of the reactors by limiting the partial pressure of the hydrocarbon compound. The invention makes it possible to use lower $O_2$/hydrocarbon reactant ratios at the reactor inlet, the remainder of the oxygen necessary for the reaction being introduced by the injection devices.

In the case of the reactions for the oxidation of methanol to give formaldehyde or dimethoxymethane and for the oxidation of ethanol to give acetaldehyde or diethoxyethane, the catalysts which may be suitable are mixed oxides, such as iron molybdenum oxides or molybdenum oxides comprising metals chosen from bismuth, vanadium, tungsten, copper, nickel or cobalt. The operating conditions are a temperature of between 200 and 350° C., preferably between 250 and 300° C., and a pressure of between 1 and 5 bar. The alcohol partial pressure can vary within a wide range from 3% to 50% and preferably from 5% to 40%, according to the type of product desired. In the case where the aldehydes are the desired products, the alcohol partial pressure is between 3% and 10% and preferably between 5% and 9%. In the case where the acetals are the desired products, the alcohol partial pressure is between 10% and 50% and preferably between 20% and 40%.

In the case of the reactions for the oxidation of ortho-xylene and naphthalene to give phthalic anhydride, the catalysts selected preferably comprise vanadium and preferably supported vanadium oxide. The operating conditions are a pressure of 1 to 5 bar and reaction temperatures of 280 to 450° C.

In the case of the reactions for the oxidation of butane, butenes, butanol and benzene to give maleic anhydride, the catalysts which are suitable comprise vanadium, in the form of supported vanadium oxide or in the form of supported mixed vanadium/phosphorus oxide. The reaction temperatures are from 350 to 500° C. and the pressures are from 1 to 5 bar.

In the case of the reactions for the oxidation of propylene to give acrolein or of isobutene or tert-butanol to give methacrolein, the catalysts which are suitable consist predominantly of molybdenum and comprise elements chosen from (but not exclusively) the following elements: nickel, iron, cobalt, tungsten, potassium, bismuth, antimony or chromium. The reaction temperatures are between 320 and 450° C. The total pressures are between 1 and 5 bar. The hydrocarbon compound partial pressures are between 5% and 15% and the $O_2$/hydrocarbon compound ratio at the reactor inlet is between 0.5 and 4, preferably between 0.8 and 2, more preferably still between 1 and 1.8 and more preferably between 1.2 and 1.6.

In the case of the reactions for the oxidation of acrolein to give acrylic acid and of methacrolein to give methacrylic acid, the catalysts which are suitable consist predominantly of molybdenum and comprise elements chosen from the following elements (but not exclusively): vanadium, tungsten, copper, antimony, niobium, strontium, phosphorus or iron. The operating temperatures are between 250 and 350° C., for a total pressure of 1 to 5 bar. The aldehyde partial pressure is between 5% and 15% and the $O_2$/aldehyde ratio at the reactor inlet is between 0.3 and 1.2 and preferably between 0.5 and 1.

Other oxidation reactions which can be carried out according to the invention are:
  The production of acrylic acid from propylene and oxygen, the coproducts being acrolein, acetic acid, maleic acid, propionic acid, acetaldehyde and acetone, for example at a temperature of 300 to 400° C. and at a pressure of 1 to 3 bar.
  The production of ethylene oxide from ethylene and oxygen, the coproducts being acetaldehyde and formaldehyde, for example at a temperature of 230 to 290° C. and at a pressure of 10 to 30 bar.
  The production of 1,2-dichloroethane from ethylene, hydrochloric acid and oxygen, the coproducts being carbon monoxide, chloral and various chlorinated compounds, for example at a temperature of 220 to 300° C. and at a pressure of 2 to 6 bar.
  The production of terephthalic acid from p-xylene and oxygen, the coproducts being maleic anhydride, o-toluic acid and benzoic acid, for example at a temperature of 175 to 230° C. and at a pressure of 15 to 30 bar.

The reactor according to the invention may also be suitable for ammoxidation reactions involving ammonia/oxygen/inert gas/hydrocarbon compound mixtures. The hydrocarbon compounds which can be used comprise propylene, isobutene, acrolein, methacrolein but also aromatic compounds. The ammoxidation reactions are carried out at a temperature from 50 to 100° C. higher than the corresponding oxidation temperatures. The reactor according to the invention makes it possible to inject one or other reactant by the injection devices. Optionally, the injected reactants can be alternated along the length of the reactor. Preferably, the oxygen (or the air/enriched air) is injected by the injection devices. Nevertheless, in the case of the ammoxidation reactions of an aldehyde, such as acrolein, the multistage injection of the ammonia by the injection devices makes it possible to limit side reactions which tend to form deposits at the reactor inlet.

By way of example, acrylonitrile (while coproducing acetonitrile, hydrocyanic acid and carbon monoxide) can be produced from propylene and/or propane, oxygen and ammonia, for example at a temperature of 400 to 500° C. and at a pressure of 1 to 4 bar.

The invention also makes it possible to carry out a fluorination process, that is to say a process for the preparation of a fluorinated compound from a chlorinated compound. Preferably, the reaction is carried out by reacting the chlorinated compound with hydrogen fluoride (HF).

The chlorinated compound can be any molecule having at least one chlorine atom and the fluorinated compound can be any molecule having at least one fluorine atom.

Preferably, the chlorinated compound is a linear or branched (preferably linear) $C_2$ or $C_3$ or $C_4$ or $C_5$ alkane or alkene comprising one or more substituents chosen from F, Cl, I and Br (preferably from F and Cl), at least one of the substituents being Cl.

Preferably, the fluorinated compound is a linear or branched (preferably linear) $C_2$ or $C_3$ or $C_4$ or $C_5$ alkane or alkene comprising one or more substituents chosen from F, Cl, I and Br (preferably from F and Cl), at least one of the substituents being F.

More particularly preferably, the chlorinated compound is a $C_3$ alkane or alkene comprising one or more substituents chosen from F, Cl, I and Br (preferably from F and Cl), at least one of the substituents being Cl, and the fluorinated compound is a $C_3$ alkene comprising one or more substituents chosen from F, Cl, I and Br (preferably from F and Cl), at least one of the substituents being F.

Alternatively, the chlorinated compound can be a $C_4$ alkane or alkene comprising one or more substituents chosen from F, Cl, I and Br (preferably from F and Cl), at least one of the substituents being Cl, and the fluorinated compound is a $C_4$ alkene comprising one or more substituents chosen from F, Cl, I and Br (preferably from F and Cl), at least one of the substituents being F.

According to one embodiment, the fluorinated compound is a hydrofluoroolefin (and thus does not comprise a Cl substituent).

Preferably, during the reaction, at least one Cl substituent of the chlorinated compound is replaced by an F substituent.

The conversion of the chlorinated compound to the fluorinated compound comprises the direct conversion (in just one stage or according to just one combination of operating conditions) and the indirect conversion (in two or more than two stages or by using more than one combination of operating conditions).

The fluorination reactions more particularly preferred are the reactions:
of 2-chloro-3,3,3-trifluoro-1-propene (HFCO-1233xf) to give 2,3,3,3-tetrafluoro-1-propene (HFO-1234yf);
of 1,1,1,2,3-pentachloropropane (HCC-240db) to give 2,3,3,3-tetrafluoro-1-propene (HFO-1234yf);
of 1,1,2,2,3-pentachloropropane (HCC-240aa) to give 2,3,3,3-tetrafluoro-1-propene (HFO-1234yf);
of 2,3-dichloro-1,1,1-trifluoropropane (HCFC-243db) to give 2,3,3,3-tetrafluoro-1-propene (HFO-1234yf);
of 1,1,2,3-tetrachloro-1-propene (HCO-1230xa) to give 2,3,3,3-tetrafluoro-1-propene (HFO-1234yf);
of 2,3,3,3-tetrachloro-1-propene (HCO-1230xf) to give 2,3,3,3-tetrafluoro-1-propene (HFO-1234yf);
of 1,1,1,2,3-pentachloropropane (HCC-240db) to give 2-chloro-3,3,3-trifluoro-1-propene (HFCO-1233xf);
of 1,1,2,2,3-pentachloropropane (HCC-240aa) to give 2-chloro-3,3,3-trifluoro-1-propene (HFCO-1233xf);
of 2,3-dichloro-1,1,1-trifluoropropane (HCFC-243db) to give 2-chloro-3,3,3-trifluoro-1-propene (HFCO-1233xf);
of 1,1,2,3-tetrachloro-1-propene (HCO-1230xa) to give 2-chloro-3,3,3-trifluoro-1-propene (HFCO-1233xf);
of 2,3,3,3-tetrachloro-1-propene (HCO-1230xf) to give 2-chloro-3,3,3-trifluoro-1-propene (HFCO-1233xf).

The fluorination reaction can be carried out with an HF molar ratio typically of 3:1 to 150:1, with a contact time of 6 to 100 s and at a pressure from atmospheric pressure to 20 bar. The temperature of the reaction can be from 200 to 450° C.

A specific example of the process which makes it possible to prepare HFO-1234yf from HFCO-1233xf occurs in the document WO 2010/123154. This process can be carried out with the reactor according to the invention.

The catalyst used for the above fluorination reactions may or may not be supported.

It can, for example, be a metal catalyst, that is to say of the elemental metal, metal oxide, metal halide and/or metal salt type, in particular a transition metal oxide or a halide or oxyhalide of such a metal.

It can in particular be antimony halide, tin halide, thallium halide, titanium halide, iron halide and a combination of these. Metal chlorides and fluorides are preferred, for example $SbCl_5$, $SbCl_3$, $SbF_5$, $SnCl_4$, $TiCl_4$, $FeCl_3$ and the combinations of these.

Other appropriate catalysts are those based on chromium, such as chromium oxyfluoride, chromium oxides, such as $Cr_2O_3$ (optionally subjected to fluorination treatments), chromium fluorides and the combinations of these.

Other possible catalysts are those based on aluminum (for example $AlF_3$, $Al_2O_3$ and aluminum oxyfluoride).

The catalyst can be chosen from fluorinated alumina, fluorinated titanium dioxide, fluorinated stainless steel, active charcoal and graphite.

It can be a mixture of chromium and magnesium (in the elemental, saline, oxide or halide form) or a mixture of chromium and another metal (in the elemental, saline, oxide or halide form).

It can also be a catalyst comprising a metal on a support. The metal can be chosen from Groups 3, 4, 5, 6, 7, 8, 9 and 13 of the Periodic Table and can in particular be Al, Cr, Mn, Co, Ni, Zn, Ti, V, Ru, Rh, Pd, Os, Ir, Pt, Zr, Mo, Re, Sc, Y, La, Hf, Cu, Ag, Au, Ge, Sn, Pb or Mg, in particular Al, Cr, Mn, Ni or Co. It can be a lanthanide (metals 58 to 71 of the Periodic Table). The metal of the catalyst can be converted into metal derivatives during its activation or its regeneration, for example into oxide, halide (fluoride, bromide, chloride), oxyhalide or pseudohalide (cyanide, cyanate, thiocyanate).

The support can be chosen from aluminum, aluminum halides and aluminum oxyhalides, alumina, activated alumina, fluorinated alumina, aluminum fluoride, active charcoal (fluorinated or non-fluorinated) and graphite (optionally fluorinated).

The catalyst can be prepared, for example, by immersion of the support in a solution of soluble compound (for example, nitrate or chloride) of the metal, or alternatively the solution can be sprayed onto the support. The support can be dried and brought into contact with a halogenating agent in the vapor form (for example, hydrogen fluoride, hydrochloric acid, chlorofluorohydrocarbon, or also $SiF_4$, $CCl_3F$, $CCl_2F$, $CHF_3$ or $CCl_2FCClF_2$) with heating in order to partially or completely halogenate the support or the metal.

Examples of supported catalysts are $FeCl_3$ supported on carbon, alumina supported on carbon, aluminum fluoride supported on carbon, fluorinated alumina supported on carbon, magnesium fluoride supported on aluminum fluoride, more generally metals (elemental metals, metal oxides, metal halides and/or metal salts) supported on aluminum fluoride, metals supported on alumina, metals supported on carbon, or the mixtures of metals.

Other examples of supported catalysts are: a magnesium halide or a zinc halide supported on $Cr_2O_3$, a chromium(III) halide supported on carbon, a mixture of chromium and magnesium (in the elemental, oxide, halide or saline form) supported on graphite, a mixture of chromium and another metal (in the elemental, saline, oxide or halide form) supported on graphite or alumina or an aluminum halide, such as aluminum fluoride.

The total metal content of the supported catalyst is preferably from 0.1% to 20% by weight, for example from 0.1% to 10% by weight (with respect to the total weight of the catalyst).

A preferred embodiment uses a specific catalyst which is a supported mixed catalyst comprising both chromium and nickel. The Cr:Ni molar ratio (with respect to the metal elements) is generally from 0.5 to 5, for example from 0.7 to 2 and in particular in the vicinity of 1. The catalyst can comprise from 0.5% to 20% of chromium and from 0.5% to 20% of nickel by weight, preferably from 2% to 10% of each metal. Reference can be made, in this regard, to the document WO 2009/118628 and in particular to the description of the catalyst from p. 4, l. 30, to p. 7, l. 16.

An advantageous catalyst is a chromium-based catalyst comprising a chromium compound of the crystalline alpha-chromium oxide type, in which from 0.05% to 6% of the atoms approximately of the alpha-chromium oxide lattice are replaced with trivalent cobalt atoms (optionally treated with a fluorinating agent). Reference is made to the document US 2005/0228202 on this subject.

The catalyst can be subjected to a fluorination. As example of fluorination, it is possible to prepare a fluorinated alumina by bringing an alumina into contact with hydrogen fluoride with heating or by spraying an aqueous hydrogen fluoride solution at ambient temperature or by immersing an alumina in solution, and by then drying. The fluorination of the catalyst may or may not be carried out in the reactor according to the invention. The temperature during the fluorination is generally from 200 to 450° C.

The catalyst can optionally comprise a low content of one or more co-catalysts, such as Co, Zn, Mn, Mg, V, Mo, Te, Nb, Sb, Ta, P and Ni salts. A preferred co-catalyst is nickel. Another preferred co-catalyst is magnesium.

For example, an unsupported chromium-based catalyst can optionally comprise a low content of one or more co-catalysts chosen from cobalt, nickel, zinc or manganese and be prepared by processes known per se, such as impregnation, mixing of powders and others.

The amount of co-catalyst, when it is present, can vary from 1% to 10% by weight, preferably from 1% to 5% by weight. The co-catalyst can be added to the catalyst by processes known per se, such as adsorption from an aqueous or organic solution, followed by the evaporation of the solvent. A preferred catalyst is pure chromium oxide with nickel or zinc as co-catalyst. Alternatively, the co-catalyst can be physically mixed with the catalyst by grinding, in order to produce a fine mixture.

Another preferred catalyst is a mixed chromium/nickel catalyst supported on fluorinated alumina. The document U.S. Pat. No. 5,731,481 describes a process for the preparation of this other catalyst.

Before activation, the catalyst is subjected to a stage of drying, preferably with a drying gas, such as nitrogen. The drying stage can be carried out at a pressure ranging from atmospheric pressure to 20 bar. The temperature of the catalyst during the drying stage can range from 20° C. to 400° C., preferably from 100° C. to 200° C.

The activation of the catalyst can preferably be carried out with HF or a fluoro- or hydrofluoroalkane and/or an oxidizing agent (preferably oxygen or chlorine). The regeneration of the catalyst can be carried out with an oxidizing agent (preferably oxygen or chlorine) and optionally HF, in one or more stages.

In order to extend the duration of deactivation of the catalyst, it is possible to add an oxidizing agent (preferably oxygen or chlorine) during the production phase, for example in a proportion of 0.05 mol % to 15 mol %, with respect to the mixture of oxidizing agent and chlorinated compound.

The temperature during the regeneration stage can be from 250 to 500° C. approximately and the pressure from atmospheric pressure to approximately 20 bar. When HF is used in combination with oxygen, the proportion of oxygen can vary from 2 mol % to 98 mol %, with respect to the HF/oxygen mixture.

The invention makes it possible in particular to carry out the injection of oxygen (or of chlorine) in situ into the reactor in the production phase and/or in the regeneration phase, and also optionally for the initial activation of the catalyst.

The invention claimed is:

1. A chemical reaction process comprising:
admission of reactants at an inlet of a reaction compartment defined between two heat-exchange plates,
withdrawal of reaction products at an outlet of the reaction compartment, and
injection of a substance into the reaction compartment,
wherein each heat-exchange plate comprises two walls defining, between them, at least one heat-exchange space, the respective walls being fixed to one another by joining regions, and the injection of substance being carried out by means of at least one substance-injecting device which passes through openings in the heat-exchange plates in respective joining regions of the plates,
wherein the reaction is of a heterogeneous catalytic type and a catalyst is positioned in the reaction compartment, and
wherein the process further comprises alternate phases of production and phases of regeneration of the catalyst, the injection of substance being carried out during the reaction phases in order to conduct a catalytic reaction in the reaction compartment and/or during the regeneration phases in order to regenerate the catalyst in the reaction compartment.

2. The process as claimed in claim 1, wherein the substance is a reactant or a catalytic compound or a compound capable of regenerating a catalyst.

3. The process as claimed in claim 1, wherein the substance is an oxygen-comprising gas.

4. The process as claimed in claim 1, wherein the substance is injected at several points of the route of the reactants in the reaction compartment.

5. The process as claimed in claim 1, wherein the process is carried out in a chemical reactor.

6. The process as claimed in claim 1, wherein the process is:
a process for dehydration of glycerol to give acrolein; or
a process for dehydration of lactic acid to give acrylic acid; or
a process for dehydration of 3-hydroxypropionic acid to give acrylic acid; or
a process for dehydration of 3-hydroxyisobutyric acid to give methacrylic acid; or
a process for dehydration of 2-hydroxyisobutyric acid to give methacrylic acid; or
a process for conversion of a chlorinated compound into a fluorinated compound; or
a selective oxidation process selected from the following:
oxidation of methanol to give formaldehyde or dimethoxymethane; oxidation of ethanol to give acetaldehyde or diethoxyethane; oxidation of ortho-xylene or naphthalene to give phthalic anhydride; oxidation of benzene, butene, butanol or butane to give maleic anhydride; oxidation of propylene to give acrolein; or oxidation of isobutene or tert-butanol to give methacrolein.

7. The process as claimed in claim 1, wherein the reaction is of heterogeneous catalytic type and a catalyst is positioned in the reaction compartment in the form of solid particles.

* * * * *